US00PP24073P3

(12) United States Plant Patent
Cummins et al.

(10) Patent No.: US PP24,073 P3
(45) Date of Patent: Dec. 10, 2013

(54) APPLE TREE ROOTSTOCK NAMED 'G.969'

(50) Latin Name: ***Malus domestica*×*Malus robusta* hybrid**
Varietal Denomination: G.969

(75) Inventors: James Cummins, Geneva, NY (US); Herbert Sanders Aldwinckle, Geneva, NY (US); Terence Lee Robinson, Geneva, NY (US); Gennaro Fazio, Geneva, NY (US)

(73) Assignees: Cornell University, Ithaca, NY (US); The United States of America, as Represented by the Secretary of Agriculture, Washington, DC (US)

( * ) Notice: Subject to any disclaimer, the term of this patent is extended or adjusted under 35 U.S.C. 154(b) by 515 days.

(21) Appl. No.: 12/925,309

(22) Filed: Oct. 19, 2010

(65) Prior Publication Data

US 2012/0096609 P1 Apr. 19, 2012

(51) Int. Cl.
*A01H 5/00* (2006.01)

(52) U.S. Cl.
USPC ..... Plt./174

(58) Field of Classification Search
USPC ..... Plt./174, 161
See application file for complete search history.

(56) References Cited

U.S. PATENT DOCUMENTS

| | | | |
|---|---|---|---|
| PP4,678 | P | 3/1981 | Carlson |
| PP7,714 | P | 11/1991 | Masseron et al. |
| PP7,715 | P | 11/1991 | Masseron et al. |
| PP8,543 | P | 1/1994 | Cummins et al. |
| PP11,070 | P | 9/1999 | Cummins et al. |
| PP12,443 | P2 | 3/2002 | Cummins et al. |
| PP17,063 | P3 | 8/2006 | Cummins et al. |
| PP17,139 | P3 | 10/2006 | Cummins et al. |
| PP18,618 | P2 | 3/2008 | Alston |
| PP21,223 | P3 | 8/2010 | Budagovsky |
| 2002/0002717 | P1 | 1/2002 | Yoshida et al. |
| 2006/0130195 | P1 | 6/2006 | Cummins et al. |
| 2006/0174386 | P1 | 8/2006 | Cummins et al. |
| 2006/0174387 | P1 | 8/2006 | Cummins et al. |
| 2010/0132081 | P1 | 5/2010 | Budagovsky et al. |

OTHER PUBLICATIONS

"Cornell Gardening Resources, Apple Tree Rootstocks," Ecogardening Factsheet #21, Cornell University, Department of Horticulture, Summer 1999, http://www.gardening.cornell.edu/factsheets/ecogardening/appleroot.html.

Cummins Nursery Catalog 2004, Rootstocks, Updated Feb. 2011, Ithaca, NY, http://www.cumminsnursery.com/rootstocks.htm.

Domoto, P., "Characteristics of Apple Rootstocks," Iowa State University, Department of Horticulture, Nov. 2004, http://www.nc140.org/2004/domotorootstock.pdf.

Norelli, J.L. et al., "Resistance of Geneva and Other Apple Rootstocks to *Erwinia amylovora*," Plant Disease, 2003 pp. 26-32, vol. 87, No. 26.

United States Department of Agriculture, Agricultural Research Service, "The National Apple Rootstock Breeding Program," Feb. 2011, Geneva, NY, http://ars.usda.gov/Main/docts.htm?docid=15654.

*Primary Examiner* — Kent L Bell
(74) *Attorney, Agent, or Firm* — MacMillan, Sobanski & Todd, LLC

(57) ABSTRACT

A new and distinct variety of apple tree *Malus domestica*× *Malus robusta* hybrid 'G.969' is described herein. The new variety is resistant to fire blight (*Erwinia amylovora*) and crown rot (*Phytophthora cactorum*). The 'G.969' rootstock is useful in that it can be propagated clonally and used as a semi-dwarfing rootstock or root system for apple trees as well as for interstems of apple trees.

5 Drawing Sheets

Genus and species: *Malus domestica*×*Malus robusta* hybrid.

Variety denomination: 'G.969'.

STATEMENT REGARDING FEDERAL FUNDING

Research related to this invention was funded under USDA ARS CRADA, Sponsor's Contract #:58-3K95-9-1358-M; the U.S. government may have rights herein.

BACKGROUND OF THE INVENTION

I. Field & Utility Summary

The present invention relates to a new and distinct variety of apple tree. The apple tree is particularly useful in that it can be propagated clonally and used as a rootstock or root system for apple trees as well as for interstems of apple trees.

II. Cultivation Summary

'G.969' originated from a planned cross in 1976 in Geneva, N.Y.

III. Comparisons

The seed parent *Malus domestica* 'Ottawa 3' is a dwarfing rootstock, i.e., trees grown on this rootstock are 30 to 35 percent the size of a standard self-rooted seedling tree. 'Ottawa 3' is known to induce good precocity to the scion (i.e., the ability to induce early reproductive development in the scion) and has high yield efficiency. 'Ottawa 3' plants produce no spines, are fairly well anchored, are a very cold hardy rootstock and have resistance to crown and root rot caused by *Phytophthora cactorum*. However, 'Ottawa 3' is susceptible to the woolly apple aphid (*Eriosoma lanigerum*) and to fire blight (*Erwinia amylovora*).

The pollen parent *Malus robusta* 'Robusta 5' is a non-dwarfing rootstock, i.e., trees on this rootstock are the same size as a standard self-rooted tree. 'Robusta 5' has a spreading tree architecture. 'Robusta 5' does not induce precocity to the scion and is not highly yield efficient. Juvenile plants of 'Robusta 5' produce many spines. 'Robusta 5' breaks buds very early in the spring and is winter hardy. It is resistant to powdery mildew (*Podosphaera leucotricha*) and fire blight, and is immune to the woolly apple aphid. Further, 'Robusta 5' has shown tolerance to the specific replant disease complex.

The 'G.969' apple rootstock of the present invention has a combination of qualities that distinguishes it from its parental plants (i.e., 'Ottawa 3' and 'Robusta 5'). For example, although 'G.969' has dwarfing properties derived from 'Ottawa 3', it is different from its dwarfing parent (i.e., 'Ottawa 3') because it produces a tree that is 45 to 55 percent of the size of a standard self-rooted seedling tree. Thus 'G.969' belongs to a different dwarfing vigor class than its 'Ottawa 3' parent. In particular, 'G.969' has dwarfing characteristics that are similar to the industry standard of *Malus domestica* 'Malling 7'. 'G.969' shares similarities with 'Ottawa 3' in that they both induce precocity to the scion, are highly yield efficient, winter hardy, and fairly well anchored.

With regard to its 'Robusta 5' parent, 'G.969' is distinguishable in that it is a dwarfing rootstock and is highly yield efficient, while 'Robusta 5' is not. However, like 'Robusta 5', 'G.969' is resistant to fire blight, powdery mildew, and the woolly apple aphid (*Eriosoma lanigerum*). 'G.969' promotes spreading habit of the scion like 'Robusta 5'. In addition, 'G.969' has been shown to have some tolerance to the replant disease complex.

As discussed above, 'G.969' is most similar to 'Malling 7' in terms of dwarfing class. However, 'G.969' is more precocious and yield efficient than 'Malling 7'.

With regard to apple tree rootstock 'G.210' (U.S. Plant Pat. No. 23,337), a variety from the same parents as 'G.969', 'G.210' produced trees that were approximately 10 to 15% more vigorous than 'G.969', when grown in the northeast United States. 'G.969' showed higher cumulative yield efficiency than 'G.210', when grown in the northeast United States. 'G.210' is more efficient at absorbing and translocating sodium to the scion leaves than 'G.969'.

With regard to apple tree rootstock 'G.935' (U.S. Plant Pat. No. 17,063), a variety from the same parents as 'G.969', G.969' is resistant to wooly apple aphid (*Eriosoma lanigerum*) and 'G.935' is susceptible.

IV. Breeding History

In the spring of 1976, pollen from a *Malus robusta* 'Robusta 5' apple tree was applied to emasculated flowers of a *Malus domestica* 'Ottawa 3' apple tree in Geneva, N.Y. In the fall of 1976, approximately 500 seeds resulting from this pollination were extracted from mature fruit derived from this cross. In the winter of 1976-77, the seeds were stratified and planted in large flats under conditions effective to germinate seeds and obtain seedlings. When germinated seedlings were about 2.5 cm tall they were inoculated with a mixture of isolates of the fungus *Phytophthora cactorum* (the causal agent of crown and root rots). The flats were flooded to mid-hypocotyl level and kept at 23° C. for one week. Surviving seedlings were transplanted into individual pots.

In the summer of 1977, each of the transplanted seedlings was inoculated with approximately $10^6$ colony forming units of the Ea 273 strain of the fire blight bacterium *Erwinia amylovora* by inserting a 26-gauge hypodermic syringe needle into the shoot tip. The seedling designated as #969 was one of the survivors of this battery of inoculations from the same cross. All the surviving plants were transplanted in Geneva, N.Y. in the fall of 1977 and allowed to grow side shoots for propagation/evaluation. In 1980, 'G.969' was evaluated for rooting ability, lack of spine production, and low root brittleness in a layering bed (stool bed). In 1983, 4 finished trees with 'G.969' rootstock were planted in a first test orchard in Geneva, N.Y. with *Malus domestica* cv. 'Golden Delicious' grafted onto this rootstock as the scion cultivar. This rootstock performed well (top 20% of many rootstocks tested) in these first test trials. In the Spring of 2002, 'G.969' and other experimental rootstocks were planted as finished trees with two scion varieties in Geneva, N.Y. and in 2003 and 2004 the orchard was spray inoculated while in bloom with fire blight and all trees of 'G.969' survived indicating good resistance of the rootstock in an orchard environment. In August of 2002, several rootstock liners of 'G.969' were budded with 15 different scion cultivars to test graft union compatibility—the test results showed that 'G.969' was compatible with all the cultivars tested. In summer 2007, 20 rootstock liners were inoculated with two different strains of fire blight (ten liners per strain) in Geneva, N.Y. As a result, the apple rootstock 'G.969' was classified as immune to one of the strains tested and moderately susceptible to the other strain of fire blight. In the fall of 2005 and 2006 tree architecture of nursery trees using 'G.969' as root stock was measured and found to promote a spreading habit (flatter branches) on diverse grafted scion varieties.

V. Asexual Reproduction

Asexual reproduction of 'G.969' has been achieved using the traditional method of clonal propagation. In particular, the original seedling of the 'G.969' was planted in Geneva, N.Y. and allowed to develop into a "mother plant." The 'G.969' mother plant was then used to obtain rooted liners using conventional layering procedures. The resulting liners were then planted in a row to generate a layering stool bed (also referred to as the "mother stool bed"). The living tissues (i.e., leaves, stems, roots, buds, and spines) of the mother stool bed were observed to be identical to secondary and tertiary stool bed plants. In addition to conventional layering, 'G.969' variety has been asexually reproduced by root cuttings, by budding and grafting onto seedling and clonal rootstocks, and by tissue culture.

VI. Stability

Observations of trees from clonal propagations indicate that all trees have proven true to type and identical in all appearances to the original tree.

SUMMARY OF THE INVENTION

'G.969' is resistant to fire blight and crown rot. It is precocious and highly productive, and useful as a dwarfing root stock. While 'G.969' rootstock is a hybrid from a cross between 'Ottawa 3' and 'Robusta 5', it is distinct from its parent cultivars in terms of dwarfing. The apple tree rootstock 'G.969' is less dwarfing than 'Ottawa 3' and more dwarfing than the non-dwarfing parent 'Robusta 5'. Unlike 'Ottawa 3', 'G.969' is resistant to fire blight. Although 'G.969' is in the same dwarfing market class as 'Malling 7', it is distinguishable from 'Malling 7' because 'G.969' is precocious and highly productive whereas 'Malling 7' is less precocious and less productive.

DETAILED BOTANICAL DESCRIPTION

Figure 1:
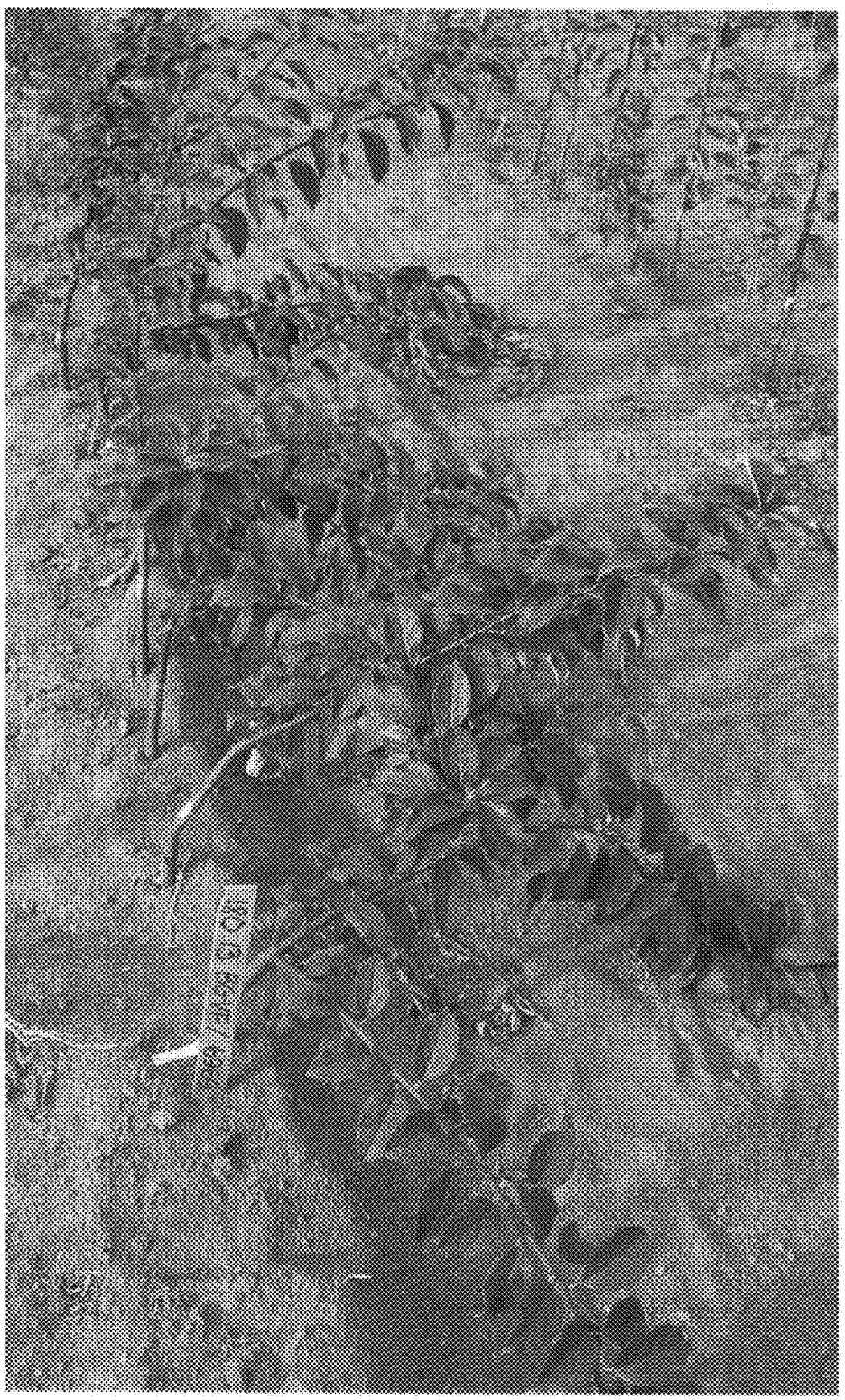
FIG. 1 shows live, budded nursery liners (including buds and bark.) The shoot shown is a fresh shoot, and is less than one year old.
Figure 2:
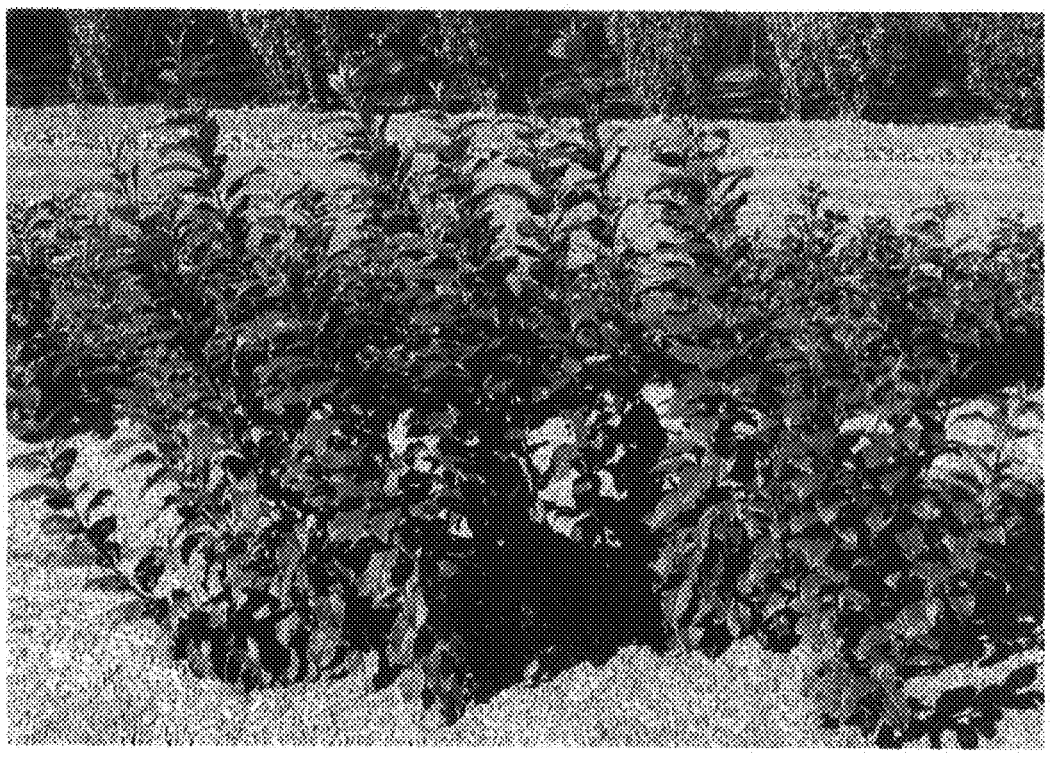
FIG. 2 shows live plants in propagation bed. The shoots shown are one year old.
Figure 3:
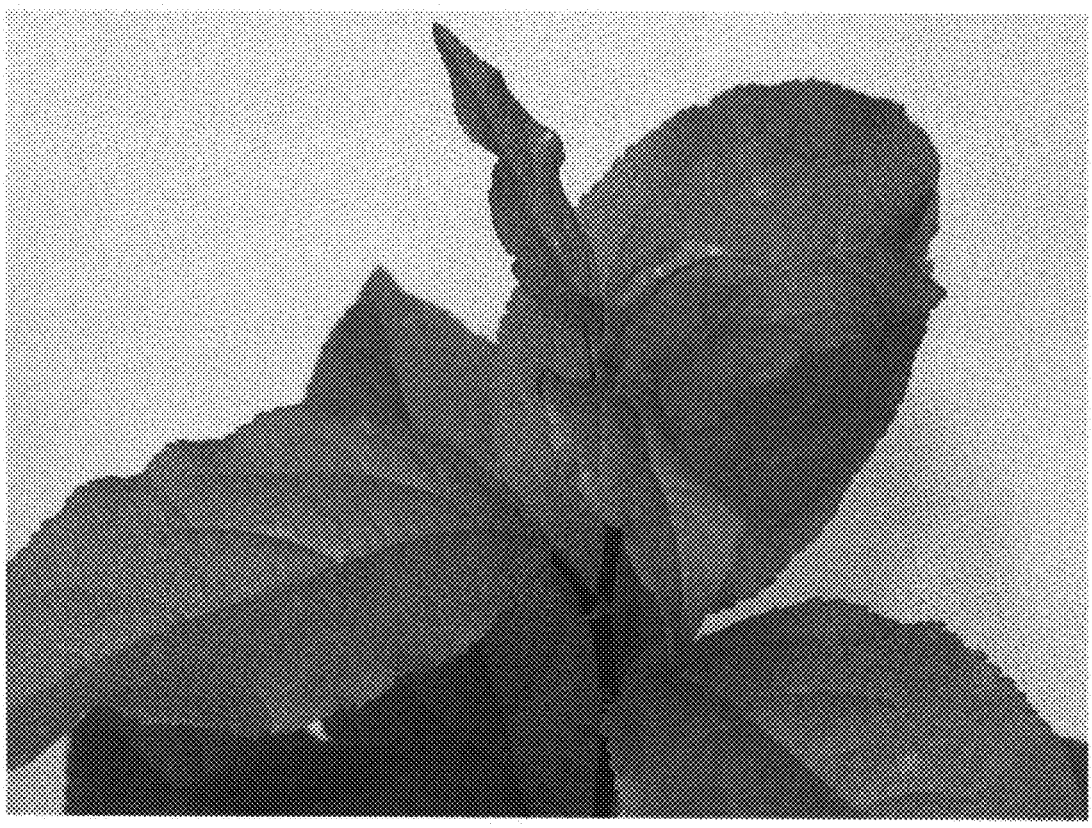
FIG. 3 shows an actively growing shoot. The shoot shown is a fresh shoot, and is less than one year old.
Figure 4:
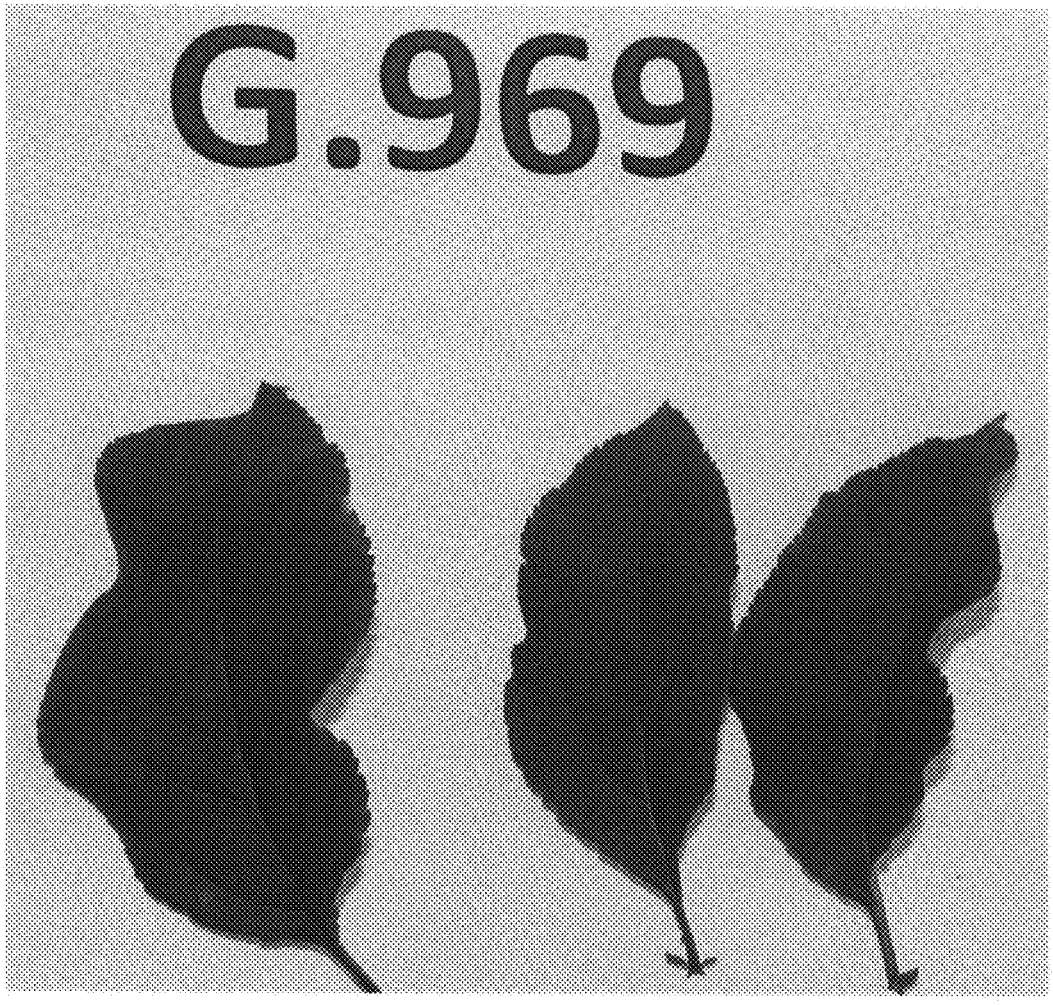
FIG. 4 shows the adaxial (upper) lamina surface of a mature leaf. The leaf shown is from a one season old plant.
Figure 5:
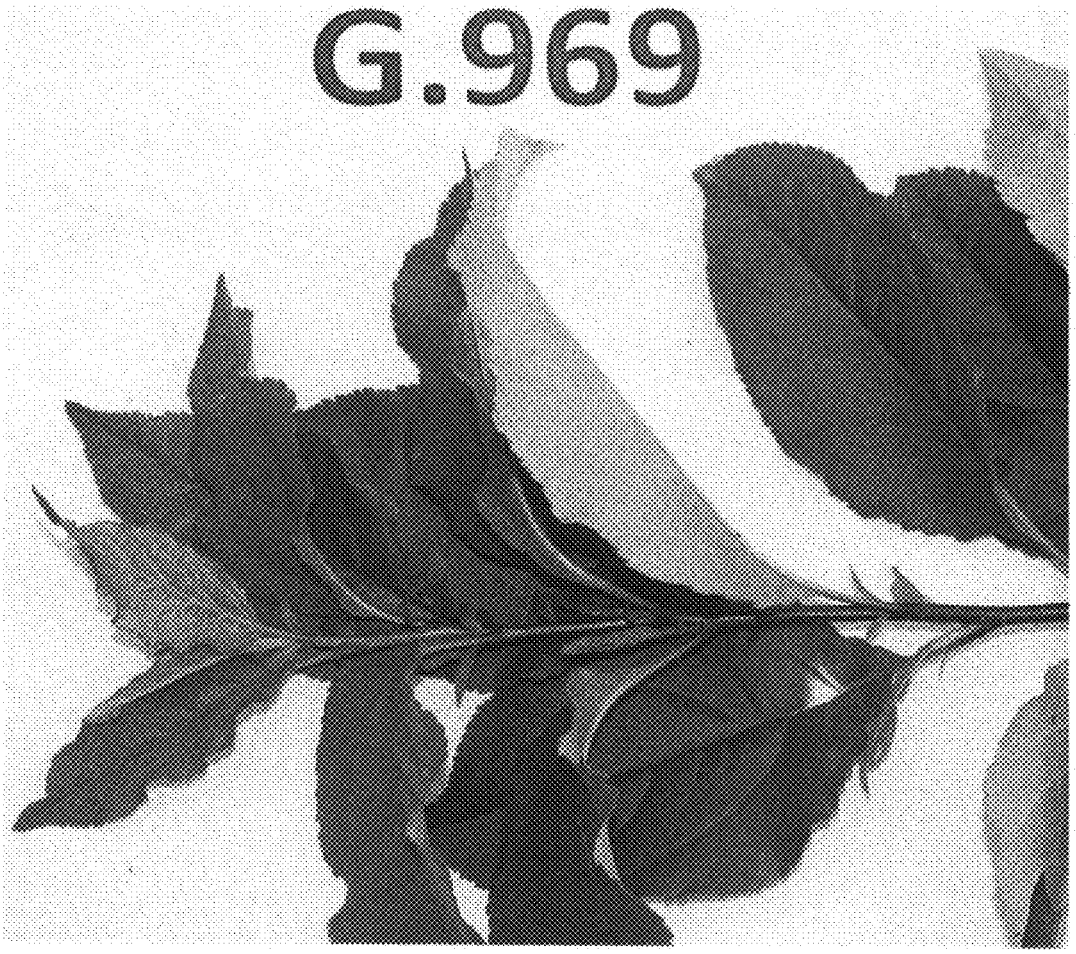
FIG. 5 shows bark, stipules and leaves on an actively growing shoot. The bark, leaves, and stipules shown is from a one year old plant.

The following description of 'G.969' contains references to color names taken from The Royal Horticultural Society Colour Chart (R.H.S.), 2001 edition. Botanical descriptions follow the Manual of Cultivated Plants (Bailey, 1949).

Tree:

*Habit.*—A self-rooted tree of 'G.969' is a small shrub typically standing about 1.5-2 meters tall by about 2 meters wide when 7 years old. There is no single dominant trunk. Instead there are few shoots arising from the crown. Very few suckers (i.e., new shoots emerging from below ground) are produced. Liners planted in the nursery stop apical growth mid season. The apical bud in these plants is pubescent Greyed-Green (RHS 191D).

*Productivity.*—In an intermediate trial performed in Geneva, N.Y., 'G.969' rootstock received the cultivar 'Empire' (*Malus domestica*) as the scion and was compared to the *Malus domestica* check rootstocks M.9 EMLA, M.26 and M.7. 'G.969' was shown to have statistically higher ($p \leq 0.05$) yield efficiency (kg yield/$cm^2$ trunk cross sectional area) than all the check rootstocks.

*Precocity.*—Scion cultivars budded on 'G.969' exhibit the same precocity as those budded on M.9.

*Fertility* (*fecundity*).—The 'G.969' plant produces flowers and fruits regularly.

Dormant shoots (buds and bark):

*Dormant mature shoots.*—Color: Greyed-Red (RHS 178A) where exposed to full sunlight grading to Greyed-Orange (RHS 173B) with diminished light exposure. Texture: Very light pubescence which gradually disappears in older tissues. Size: 30-60 cm long; may have some spines.

*Axillary buds.*—Size: 2-3 mm long and 3 mm wide with little pubescence. Shape: Obtuse, sessile, somewhat appressed and flattened. Texture: Some pubescence.

*Bark on three-year-old shoots.*—Color: Greyed-Green (RHS 197A). Lenticels: Color: Greyed-Orange (RHS 163B). Size: 0.3-0.4 mm in diameter. Quantity: 1-2 lenticels per $cm^2$.

Leaves:

*Mature leaves.*—Leaf arrangement: Alternate. Shape: Simple, recurved, oblong-ovate. Size: Length: 85 mm. Width: 50 mm at the widest point. Laminae: Somewhat wavy. Apex: Acuminate. Base: Nearly symmetrical rounded. Margin: Acutely serrated, with about 5 serrations per cm. Upper surface: Color: Green (RHS 126B). Texture: Glabrous and translucent. Lower surface: Color: Green (RHS 146C). Texture: Somewhat pubescent. Venation: Netted. Leaf poise: 15°-25° from the shoot, depending on shoot orientation. Stipules: Length: 8 mm. Width: 2 mm. Petioles: Diameter: 2 mm. Color: Gradation of Green (RHS 140A) to Greyed-Red (RHS 179A) depending on low or high exposure to light.

Disease resistance: As described above, 'G.969' exhibits resistance to fire blight. The percent lesion measured after inoculation of potted liners in the greenhouse using different strains of *E. amylovora* was negligible for two of the strains and moderate for the other two, indicating a specific resistance to the bacterium. 'G.969' has survived inoculation with *Phytophthora cactorum* crown and root rot, indicating resistance.

We claim:

1. A new and distinct variety of apple tree named 'G.969' herein described and illustrated.

* * * * *